United States Patent [19]

Hass

[11] Patent Number: 4,964,769
[45] Date of Patent: Oct. 23, 1990

[54] AIR-ISOMETRIC TEMPOROMANDIBULAR JOINT AND VERTICAL CLOSURE JAW RELATOR APPARATUS

[76] Inventor: Martin M. Hass, 1055 El Medio Ave., Pacific Palisades, Calif. 90272

[21] Appl. No.: 348,600

[22] Filed: May 4, 1989

[51] Int. Cl.⁵ .............................................. A61C 9/00
[52] U.S. Cl. ...................................... 433/214; 433/69
[58] Field of Search ....................... 433/68, 69, 70, 71, 433/215, 214, 43

[56] References Cited

U.S. PATENT DOCUMENTS

| | | | |
|---|---|---|---|
| 1,589,973 | 6/1926 | Landa | 433/68 |
| 1,776,474 | 9/1930 | Messerman | 433/68 |
| 2,245,288 | 6/1941 | Moylan | 433/69 |
| 2,309,270 | 1/1943 | Opotow | 433/68 |
| 2,582,104 | 1/1952 | Coble | 433/69 |
| 2,841,871 | 7/1958 | Miller | 433/68 |
| 3,084,435 | 4/1963 | Hass et al. | 433/214 X |
| 3,293,748 | 12/1966 | Skinner | 433/68 |
| 4,526,543 | 7/1985 | Hass | 433/214 |

Primary Examiner—John J. Wilson
Assistant Examiner—Nicholas D. Lucchesi
Attorney, Agent, or Firm—Matthew F. Jodziewicz

[57] ABSTRACT

An apparatus for producing a desired balanced vertical jaw closure in a human mouth. First and second platform members, each capable of being respectively mounted in a fixed, known relation on the upper and lower jaws in spaced, vertically aligned juxtaposition are provided. A closed-air cell spacer member is connected between the platform members for providing an adjustable isometric pressure resistance against vertical closure of the jaws. A selectively movable piston action pin member is also connected between the platform members for selectively controlling the rest-close vertical relationship desired between the mounted platform members to protect against overclosure and damage to the ear canal and blood circulation to the cranium.

5 Claims, 3 Drawing Sheets

AIR-ISOMETRIC TEMPOROMANDIBULAR JOINT AND VERTICAL CLOSURE JAW RELATOR APPARATUS

BACKGROUND OF THE INVENTION

1. Field of the Invention:

This invention relates to a method and an apparatus for balancing the structure of a human mouth to function in harmony with artificial dentures which have been previously manufactured, for balancing the biting surface of natural human teeth in the jaws, or for balancing an artificial denture during or after its design or manufacture, and, in particular, to a method and an apparatus for balancing the temporomandibular joints of a human mouth in relation to the vertical closure of the jaws. The method and apparatus of the invention may be used with natural teeth, single denture plates, full denture plates, immediate dentures and bite-opening splints for temporomandibular joint treatments where an unbalanced bite has caused joint pains, hearing problems, headaches or the like.

2. Description of the Related Art:

Disease of the temporomandibular joint (TMJ) is often undiagnosed or misdiagnosed because it mimics many different diseases and has such a wide variety of symptoms.

Most people who have this problem suffer from a myo-facial pain-dysfunction syndrome primarily as a muscle problem related to dental or skeletal malrelationships and tensional factors, or in some cases, as a reversible irritation in the temporomandibular joint. Most of these patients can be successfully treated using nonsurgical techniques if the symptoms are correctly diagnosed and treatment follows early in the disease. Failure to properly diagnose and treat the disease early, however, usually results in progressive organic disease spreading within the joint, usually osteoarthritis. The latter often requires some form of surgical treatment.

The present invention offers a form of treatment that avoids the trauma of surgery and offers instead a quick and non-traumatic procedure which can be done to permanently and accurately correct the balancing of the temporomandibular joint and associated jaws and teeth in the mouth.

Prior art, such as U.S. Pat. No. 4,526,543 issued to the present inventor, has proven that the procedure of balancing the temporomandibular joint and jaws by correcting the mating of the occlusal surfaces of the teeth in the mouth is successful in treatment of temporomandibular joint disease and its attendant symptoms.

The present invention improves upon this prior art by providing a method and apparatus capable of use by a dental technician and requiring only minimal professional supervision to ensure its proper functioning and treatment.

The present invention also provides both a method and apparatus that is quicker in treatment than those methods or apparatus of the prior art.

SUMMARY OF THE INVENTION

These advantages, and others, are preferably achieved in a preferred apparatus of the invention for producing a desired vertical jaw closure while balancing both of the temporomandibular joints in a human mouth and comprises first and second annular, flat support members. Each of the support members is adapted to fit into the human mouth and be mounted upon the upper and lower jaws, respectively, in a spaced, vertically aligned, juxtaposition, that is, one superimposed over the other.

Each of the support members has a protrusion on its forward periphery for purposes that will be discussed below.

Each of the support members also has pivotally mounted thereon a pair of arm members adapted to swing in an arcuate fashion outwardly therefrom. These arm members are adapted to engage its respective jaw to hold its support member in a removable, but fixed, known relation to the jaw upon which it is mounted.

Means are operatively connected between the first and second support members for providing an adjustable isometric pressure resistance against vertical closure of the jaws.

Means are also operatively connected between the first and second support members for limiting the maximum vertical closure between the first and second support members mounted in spaced, vertically aligned, juxtaposition in the mouth.

A preferred method of the invention for producing a desired vertical jaw closure while balancing both of the temporomandibular joints in a human mouth, comprises the steps of mounting a first adjustable support platform to the upper jaw of a human mouth in a fixed, but removable, relation so that the occlusal surfaces of the teeth of the upper jaw are uncovered. A second adjustable support platform is similarly mounted to the lower jaw of the mouth so that the first and second adjustable support platforms are in spaced, vertically aligned, juxtaposition within the mouth. The occlusal surfaces of the teeth of the lower jaw are likewise uncovered.

A desired isometric pressure resistance against the vertical closing of the support platforms (and the jaws upon which they are mounted) is selected.

Likewise, a desired maximum vertical closure between the support platforms (and the jaws upon which they are mounted) is also chosen.

The occlusal surfaces of the teeth on both the upper and lower jaws are covered with a conformable substance that hardens to a permanent conformed shape upon curing.

The upper and lower jaws are then urged to chew naturally against the chosen desired isometric air pressure resistance and to close during chewing to the desired maximum vertical closure distance.

The support platforms are removed from the mouth after the conformable substance has either hardened or been conformed to the specific structural configuration of the mouth. At this time, the jaw alignment and patient chew accuracy can be tested and verified.

A better understanding of the invention, as well as the fabrication and use of its components, may be had from a consideration of the following description of some exemplary preferred embodiments thereof, particularly when read in conjunction with the appended drawings, in which:

DETAILED DESCRIPTION OF THE DRAWINGS

DESCRIPTION OF THE PREFERRED EMBODIMENTS

Figure 1:
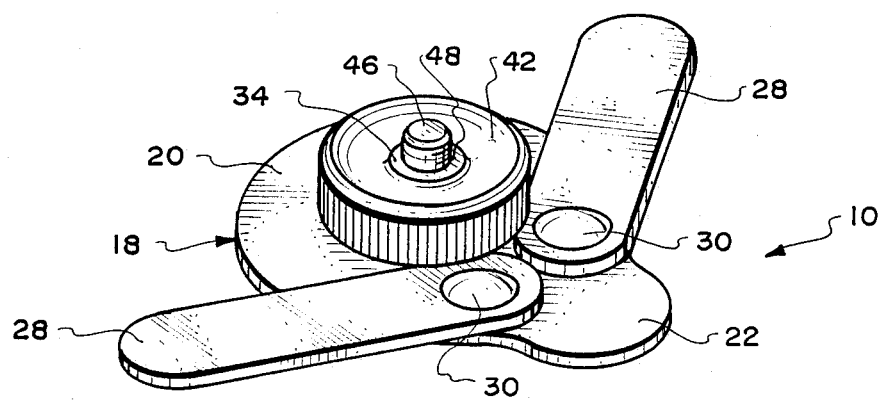
FIG. 1 is a side perspective view of an apparatus embodying the present invention.
Figure 2:
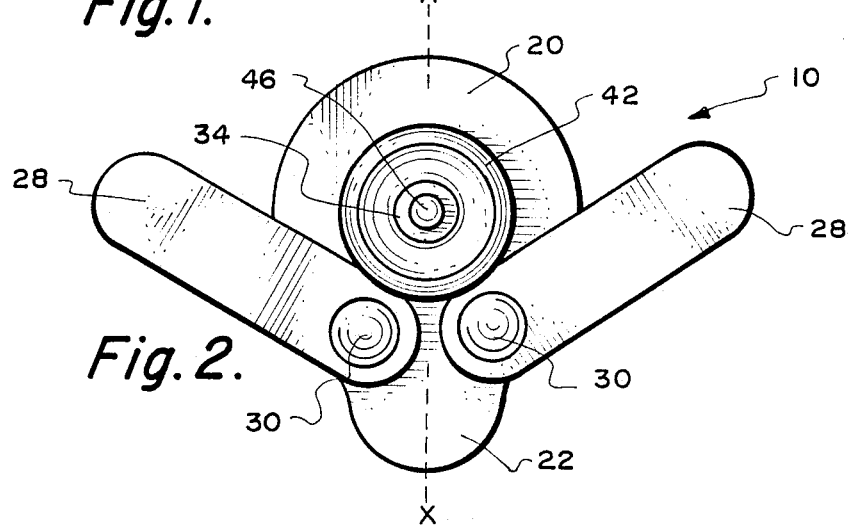
FIG. 2 is a top plan view of the apparatus of the invention as it would be in position in the mouth for balancing the teeth and bone structure.
Figure 3:
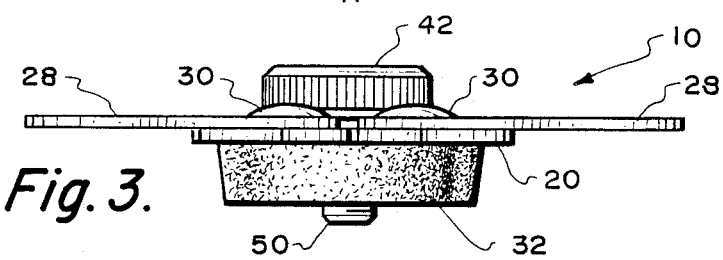
FIG. 3 is a frontal plan view of the apparatus of the invention.

The preferred embodiment of the apparatus of the invention as illustrated in the drawings, for producing a desired vertical jaw closure while balancing both of the temporomandibular joints (TMJ) in a human mouth, includes first and second annular, flat support members 10 and 12, respectively. Each of the support members is adapted to fit into the human mouth and be mounted upon the upper and lower jaws, 14, 16, respectively, of the human mouth in spaced, vertically aligned juxtaposition, as best illustrated in FIGS. 5 through 9.

Figure 4:
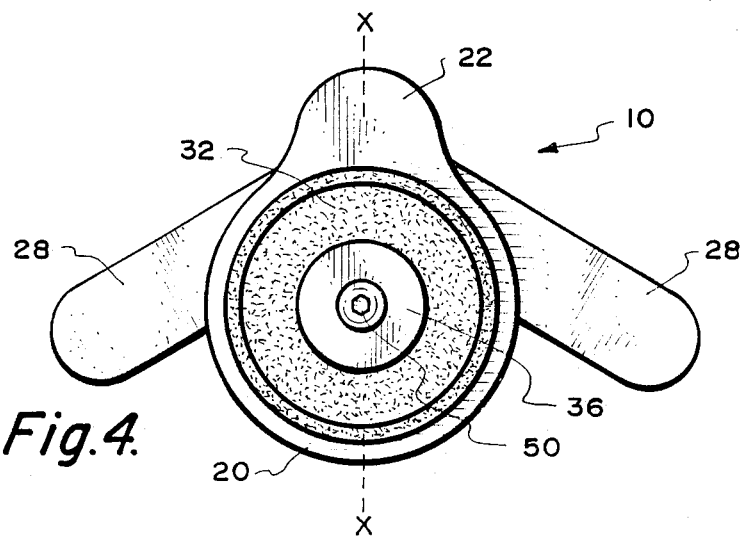
FIG. 4 is a bottom plan view of the apparatus of the invention.

The first, or upper support member 10, illustrated in FIGS. 1 to 4, will be described in detail. Upper support member 10, has a bearing plate 18, comprising a substantially circular main body section 20. At one end of this main circular section 20, is a substantially semi-circular protrusion 22, which is adapted to be seated in the center portion of the mouth. An aperture 26, is located at about the center of main body section 18. The projected longitudinal axis X—X passing through protrusion 22, extends through the center of aperture 26 as best seen in FIG. 4.

Arms 28, 28, may be mounted for pivotal movement on the planar surface of bearing plate 18 in a plane parallel to the plane of bearing plate 18, by conventional means, such as rivets 30, 30, in bearing plate 18 of support member 10. Preferably, rivets 30, 30, are spaced equally from longitudinal axis X—X and are equally radially spaced from the center of main body section 20.

Each of the pivotally mounted arms 28, 28, is of a dimension and position such that it may be extended in an arcuate fashion beyond the edge of its respective support member. Specifically, as in the illustrative embodiment shown in the drawings, arms 28, 28, are located adjacent each other near the base of protrusion 22, located at the forward portion 24, of main body portion 20, of its support member. Arms 28, 28, extend in a generally rearward direction and may be swung outwardly from longitudinal axis X—X of the main body portion 20, of the support member sufficient to seat at the edges of the patient's mouth, dentures or denture bases. Of course, the pivotal arrangement permits adjustment of the support member to mouths of varying configurations or sizes.

A flexible, resilient spacer member 32, having a generally circular shape, is mounted on support member 10, in a selectively removable manner by conventional means, such as threaded pin 34, having an enlarged head portion 36, and an extended opposite end portion 38, adapted to pass through an aperture 40, of spacer member 32, and be received and retained in aperture 26, in bearing plate 18, by a threaded nut 42. In use, enlarged head portion 36, of pin 34, engages spacer member 32, and retains it in a fixed but selectively removable relation to support member 10, by threaded pin 34, and providing a threaded adjustment by nut 42, that permits a selective isometric pressure to be exerted upon and throughout spacer member 32, for purposes better discussed below.

When spacer member 32, is to be removed from support member 10, pin 34, is threadably withdrawn from aperture 26, thereby releasing spacer member 32, from engagement with the planar surface of support member 10. End portion 36, of pin 34, is now withdrawn from aperture 26, of spacer member 32, and a replacement spacer member may be used by inserting pin 34, through the aperture, in the replacement spacer member and then into aperture 26, in support member 10. Spacer member 32, may be removed for hygienic or wear replacement purposes. The air cushions are disposable for hygienic and sterilization purposes.

Flexible, resilient spacer member 32, may be formed from resilient closed cell material and, in the preferred embodiment, may be fabricated from closed cell polyethylene or any similar suitable Federal Food and Drug Administration biocompatible material of sufficient thickness to abut both support members 10 and 12, when the support members are in spaced, vertically aligned, juxtaposition in the mouth. A preferred thickness would be about 5/16 of an inch.

Resilient spacer member 32, uses the confined gas (usually air) in its closed cell structure to exert and transmit a pre-determined isometric, or even resistence to compressive forces applied to it, due to the known fact that a confined gas exerts pressure equally throughout its free volume. An adjustment may be made to close the jaws to a proper rest-close relationship by adjusting the threaded nut 42, along pin 34, so that the enlarged head end 36, of pin 34, is threadably advanced or withdrawn along pin 34, thereby producing a predetermined, but isometric pressure throughout spacer member 32.

While it is preferred that spacer member 32 be circular in its configuration, other configurations are also possible as long as they do not extend to cover the occlusal surfaces of the teeth when in position in the mouth.

Note also that the counter balacning effect of the air cushion protects against denture base tilting, as the patient chews against the center bearing air resistance at the proper rest-close vertical relationship.

Second support member 12, mates with first support member 10, and is of a similar construction to that discussed above, except that it comprises no structure for retaining a spacer member, but has instead a simple bearing plate 44, upon which spacer member 32, engages and supplies a mating base upon which the selected isometric pressure resistance of spacer member 32, can be applied against vertical closure of the two supporting members 10 and 12, and, hence jaws 14, 16, upon which the support members 10 and 12 are each fixed, to produce an even muscle pull and jaw bracing at a proper rest-close vertical relationship.

Figure 5:
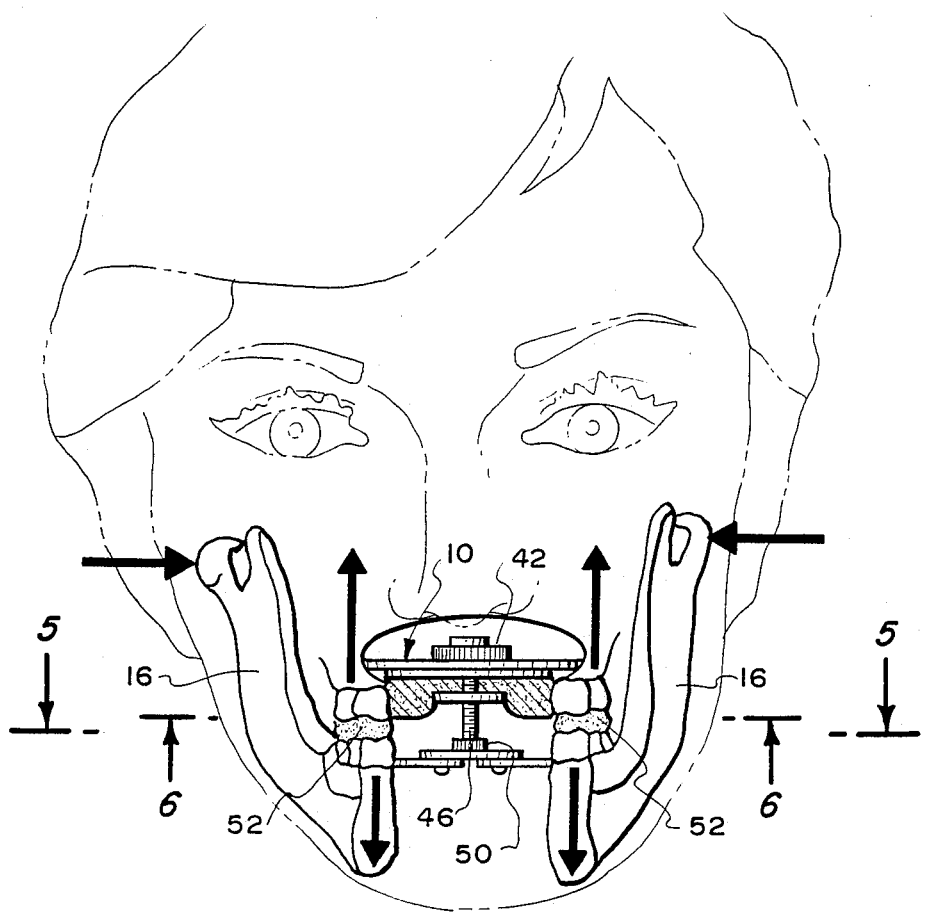
FIG. 5 is a cross-sectional view of the apparatus of the invention showing, in phantom line, a patient having the apparatus of the invention in position for balancing the mouth structure.
Figure 8:
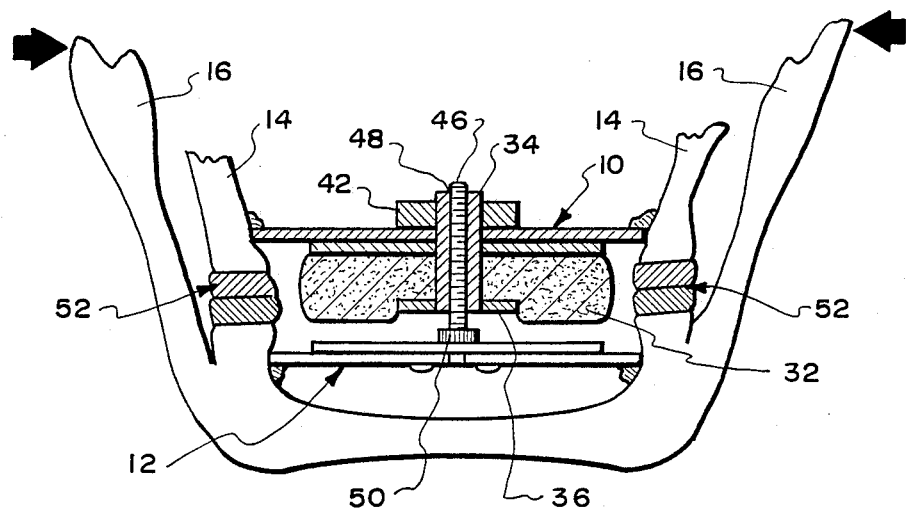
FIG. 8 is a simplified cross sectional view similar to FIG. 5 emphasizing the apparatus of the invention in position in a human mouth in relaxed position.
Figure 9:
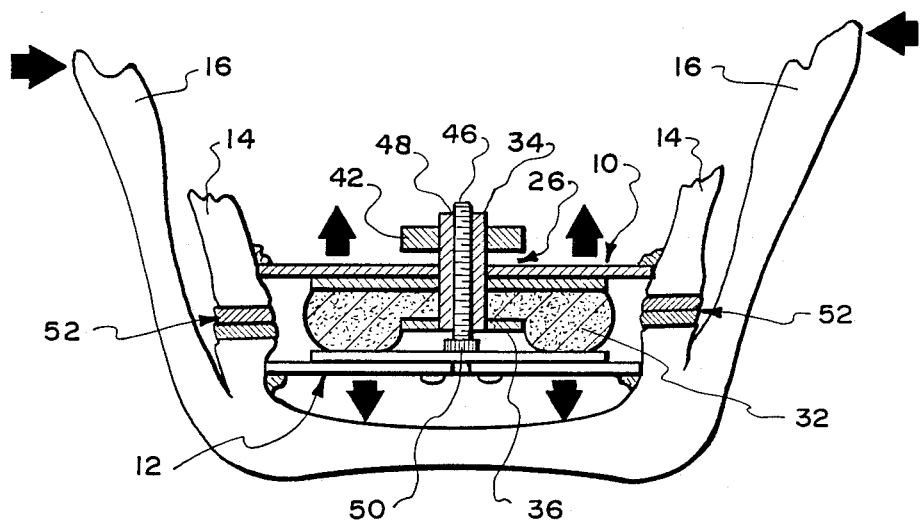
FIG. 9 is a simplified cross sectional view similar to FIG. 8 emphasizing the apparatus of the invention in position in a human mouth under biting pressure.

Means are operatively connected between support members 10, 12, for selectively limiting the maximum vertical closure between support members 10, 12, when the support members are mounted in spaced, vertically aligned, juxtaposition in the mouth as illustrated in FIGS. 5, 8 and 9.

A prefered structure for accomplishing this is a threaded second pin member 46, adapted to be threadably received through a threaded passageway 48, in pin 34, and having an end 50, adapted to engage and abut second support member 12, to selectively limit the maximum vertical closure between support members 10 and 12, when the support members are in spaced, vertically aligned juxtaposition in the mouth.

In practice, second pin 46, can be threadably advanced or retreated in passageway 48, so that its end 50, abuts the planar surface of bearing plate 18, of support member 12, at the maximum desired vertical closure distance of jaws 14, 16, and thus prevents any further lessening of the closure distance between the jaws. It should be noted that vertical closure is controlled by this dialing pin, while the isometric air pressure resistance remains the same. Also, the dialing pin contacts the lower platform while the patient is in rest position, which is constant.

The manner in which the apparatus of the present invention is inserted into the mouth for use is best seen in FIGS. 5 through 9. It will be noted from the drawings that support members 10, 12, may be positioned on jaws 14, 16, by having adjacent arms 28, 28, removably fixed, on the side of the jaws adjacent to the patient's roof and floor of the mouth.

The edge of each arm 28, 28, is temporarily secured to the jaw by sealing, sticky or adhesive wax which secures the end of each arm to the jaw, via plints, dentures, or denture bases.

Similarly, a piece of wax is used to secure protrusion 22, to the forward central portion 24, of each jaw.

Figure 6:
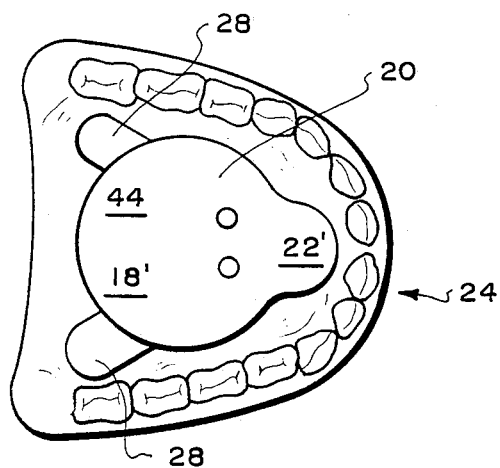
FIG. 6 is a view along the line 5—5 in the direction of the arrows shown.
Figure 7:
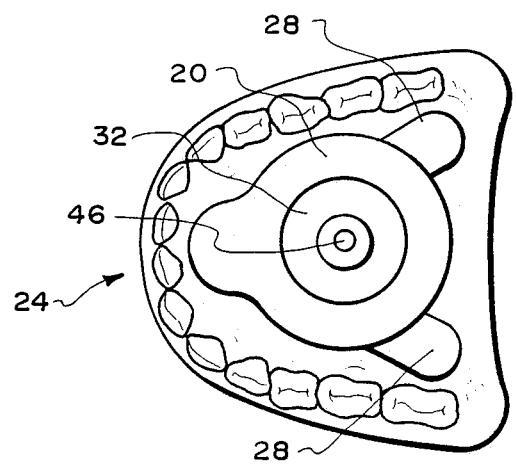
FIG. 7 is a view along the line 6—6 in the direction of the arrows shown.

It is thus seen that each support member is secured and supported at these three points to its respective upper or lower jaw, thus providing a stable tripod mount. These three fixation points, as may be seen in FIGS. 6 and 7, are at the extreme ends of arms 28, 28, which are supported on opposite sides at the rear of the mouth near the molars, while front protrusion 22, is supported at the central forward portion 24, of the mouth in back of the teeth. Preferably, protrusion 22, is placed at the center of the mouth, whereas arms 28, 28, are placed on opposite sides of the mouth and equally spaced from longitudinal axis X—X.

It will, of course, be apparent that the apparatus of the invention being described herein is equally capable of use with existing dentures or for bite correcting splints on natural teeth. In any of these applications or models of operation, the support members 10, 12, are used in substantially the same manner as shown in the drawings and described above.

In cases involving existing dentures, the support members may be attached to the dentures as opposed to the denture bases that are used for the construction of new dentures.

When dentures are being fitted to customize the chew-in occlusion of the dentures, the upper and lower denture bases are placed into the patient's mouth. The support members are anchored to the dental bases in spaced, vertically aligned, juxtaposition to on another, as seen best in FIGS. 5, 8 and 9.

The uncovered occlusal surfaces of the teeth, jaws or dental plates, are then covered with a layer 52, of a biocompatible substance which is applied in a soft conformable state, but which sets up to a hardened conformed state in a relatively short time period.

As a non-limiting example, such a biocompatible material includes, but is not limited to, wax, or to dental soft acrylic that can be light cured, self cured or pressure cured. While the thickness of the layer of biocompatible material must, of necessity, vary from patient to patient, it is preferred to have this layer vary from about 1 mm to about 3 mm in thickness.

Once support members 10, 12, are in place, the air resistance pressure is activated in spacer member 32, against the closure forces exerted by the jaws in chewing downward. This is accomplished by threadably advancing or retreating nut 42, along pin 34, so as to exert pressure via enlarged head end 36 of pin 34, against spacer member 32, positioned between two support members 10, 12.

A second vertical adjustment is made to the apparatus to chose a rest-close relationship between the two support members during chewing.

This is accomplished by threadably advancing or retreating pin 46, through passage 48, in pin 34, so as to permit its head end 50, to engage contact or abut the planar surface of support member 12, at the patient's constant vertical rest position distance between the two support members, and thus prevent any further lessening of this distance.

Once support members 10, 12, and layer 52, of conformable material are in place, the patient is instructed to bite down and chew naturally against the resistance of spacer member 32, positioned between support members 10, 12.

As stated previously, it is a known general law of physics that a confined gas, such as the gas confined in the closed air cell structure of the flexible, resilient spacer member 32, when subjected to pressure will exert equal, isometric pressures in all directions. Accordingly, when the patient bits down and chews naturally on the flexible, resilient spacer member 32, the air resistance will naturally seat the denture bases evenly, and drive the soft conformable layer 52, of material placed thereon, against one another. This will tend to conform layer 52, to provide a balanced and matched closure pattern between jaws 14, 16, thus balancing the jaw muscles as well as bracing condyles of the jaw evenly in their sockets without further need for corrective measures.

With the mouth system in balance, the soft conformable material on the occlusal surfaces is automatically engraved, patterned and molded to a perfectly balanced chew-in occlusion while in the patient's mouth by the patient's own chewing action. This material is now allowed to harden in this permanently conformed shape (in the case of a self-curing tooth acrylic, the material hardens while the patient chews, within a matter of minutes). In the case of wax, the wax can be chilled, tested and verified directly in the mouth (without the TMJ aligned).

The hardened bite pattern is tested in the patient's mouth to verify both the chewing and the rest-close accuracy. The even distribution of pressure helps to promote TMJ health, chewing efficiency, denture stability and comfort.

A proper jaw closure helps protect against damage to the ear canal, loss of hearing, and impairment of blood circulation to the head areas. A balanced muscle function guards against muscle spasms that can cause the bones of the cranium, as well as the neck muscle attachment to shift and cause pains.

The patient now has a customized chew-in occlusion perfectly balanced to the unique characteristics of his mouth that functions in harmony with his or her mouth-joint system. Also, it does not require repeated, time consuming bite re-checks, adjustments, or, in the case of dentures, the necessity of sending the dentures back to the laboratory for tooth re-sets, re-articulations and re-processing, all of which have the potential for introducing errors and expense into the denture making process.

It will be noted that the present method and apparatus is particularly applicable to the balancing of natural teeth or finished dentures as well as to the original fabrication of dentures. The present method relies upon the natural centering of the jaws without any restraints other than the air pressure restraints of closing. No forward-backward, anterior-posterior or lateral restraint is placed upon the jaws, so the jaws will automatically function, brace, and chew instinctively and naturally. The present method uses no tubes or other apparatus protruding fron the front of the mouth, or covering the occlusal surfaces of the teeth, but relies upon the basic reflexes of chewing and bracing against air resistance which, when undisturbed by other contacts, will automatically position the jaws in their best functional, working alignment.

In practice, the balancing method disclosed herein finds its greatest application to the balancing of the tooth occlusion of existing dentures, TMJ splints, or even natural teeth that do not contact evenly upon bite closure. This results from the fact that, since teeth can shift position, especially after a tooth extraction, the resulting tooth-hinge, mis-match can cause a TMJ dysfunction, with its related temporal mandibular joint pains and problems that can affect any part of the body. For a person wearing dentures, a bite overclosure can affect both the appearance, the hearing capabilities and gum shrinkage. It is therefore desirable that periodically, as frequently as once a year, for example, a person's jaw alignment should be tested and adjusted by air-aligning the bite, if necessary, to prevent a malocclusion that could cause a loosening of natural teeth, bridges, dentures, or a TMJ dysfunction. In the case of immediate dentures, where there is considerable bone change in the first few months, the apparatus of this invention can also be used during the course of relining the dentures in addition to restoring the TMJ Hinge, tooth, and muscle harmony.

Skilled practitioners will recognize that the particular embodiments discussed and illustrated herein are exemplary in nature, so that many modifications thereof are possible in terms of materials, construction and application, depending upon the particular problem at hand. Accordingly, the scope of of the present invention should be limited only by the claims appended hereinafter.

I claim:

1. An apparatus for producing a desired vertical jaw closure while air balancing both the muscle action and temporomandibular joint function during chewing, in a human mouth, comprising:

a first and a second annular, flat support member, each adapted to fit into the human mouth and be mounted upon the upper and lower jaws, respectively, of the human mouth in spaced, vertically aligned juxtaposition, each having a protrusion on its periphery and each further having pivotally mounted thereon a pair of arm members adapted to swing in an arcuate fashion outwardly therefrom for engaging the upper and lower jaws to hold its respective support member in a fixed, known relation to the jaw which it is mounted;

means operatively connected between said first and second support members for providing an adjustable isometric air pressure resistance during vertical closure of the jaws; and means operatively connected between said first and second support members for selectively controlling the minimum rest-close vertical closure possible between said first and second support members mounted in spaced, vertically aligned juxtaposition in the mouth.

2. An apparatus as in claim 1 wherein said means operatively connected between said first and second support members for providing an adjustable isometric air pressure resistance during vertical closure of the jaws, comprises:

a central aperture in said first support member;

a flexible, resilient spacer member fabricated from a biocompatible closed-air cell material having an aperture therethrough, said aperture in said spacer member adapted to receive and retain therein a first pin having a first enlarged head end adapted to engage and retain said flexible, resilient spacer member in an abutting relation therewith and an opposite second end adapted to be received and retained in said central aperture of said first support member in a selectively removable friction fit, said spacer member having sufficient thickness to abut both said first and second support members when said support members are in spaced, vertically aligned juxtaposition in the mouth.

3. An apparatus as in claim 2 wherein said means operatively connected between said first and second support members for selectively controlling the rest-close vertical closure between said first and second support members mounted in spaced, vertically aligned juxtaposition in the mouth, comprises:

a threaded second pin member adapted to be threadably received through a threaded passageway in said first pin and having an end adapted to engage said second support member to selectively limit the maximum vertical closure between said first and second support members when said support members are in spaced, vertically aligned juxtaposition in the mouth.

4. An apparatus for producing a desired vertical jaw closure while air balancing both the muscle action and temporomandibular joint function during chewing, in a human mouth, comprising:

a first and a second annular, flat support member, each adapted to fit into the human mouth and be mounted upon the upper and lower jaws, respectively, of the human mouth in spaced, vertically aligned juxtaposition, each having a protrusion on its periphery and each further having pivotally mounted thereon a pair of arm members adapted to swing in an arcuate fashion outwardly therefrom for engaging the upper and lower jaws to hold its respective support member in a fixed, known relation to the jaw upon which it is mounted;

means operatively connected between said first and second support members for providing an adjustable isometric air pressure resistance during vertical closure of the jaws; and means operatively connected between said first and second support members for selectively controlling the rest-close vertical closure between said first and second support members mounted in spaced, vertically aligned juxtaposition in the mouth, including;

a central aperture in said first support member;

a flexible, resilient spacer member fabricated from a biocompatible closed-air cell material having an aperture therethrough, said aperture in said spacer member adapted to receive and retain therein a first pin having a first enlarged head end adapted to engage and retain said flexible, resilient spacer member in an abutting relation therewith and an opposite second end adapted to be received and retained in said central aperture of said first support member in a selectively removable friction fit, said spacer member having sufficient thickness to abut both said first and second support members when said support members are in spaced, vertically aligned juxtaposition in the mouth; and, a threaded second pin member adapted to be threadably received through a threaded passageway in said first pin and having an end adapted to engage said second support member to selectively limit the maximum vertical closure between said first and second support members when said support members are in spaced, vertically aligned juxtaposition in the mouth.

5. A method for producing a desired functional chewing vertical jaw closure while air aligning both of the temporomandibular joints in a human mouth, comprising the steps of:

mounting a first adjustable support platform to the upper jaw of a human mouth in a fixed removable relation so that the occlusal surfaces of the teeth of the upper jaw are uncovered;

mounting a second adjustable support platform to the lower jaw of a human mouth in a fixed removable relation so that said first and second adjustable support platforms are in vertically aligned juxtaposition with the mouth and the occlusal surfaces of the teeth of the lower jaw are uncovered;

selecting a desired isometric air pressure resistance against the vertical closing of said first and second support platforms and the jaws upon which they are mounted;

selecting a desired rest-close vertical relationship between said first and second support platforms;

covering the occlusal surfaces of the teeth on both said upper and lower jaws with a conformable substance that can be hardened to a permanent conformed shape;

urging the upper and lower jaws to chew naturally against said desired isometric air pressure resistance and to close to said desired rest-close vertical relationship;

removing said first and second support platforms from the mouth after said conformable substance has hardened.

* * * * *